US010980417B2

(12) United States Patent
Shen

(10) Patent No.: US 10,980,417 B2
(45) Date of Patent: Apr. 20, 2021

(54) ACUTE CARE ECO SYSTEM INTEGRATING CUSTOMIZED DEVICES OF PERSONALIZED CARE WITH NETWORKED POPULATION BASED MANAGEMENT

(71) Applicant: Michael Shen, fort lauderdale, FL (US)

(72) Inventor: Michael Shen, fort lauderdale, FL (US)

(*) Notice: Subject to any disclaimer, the term of this patent is extended or adjusted under 35 U.S.C. 154(b) by 993 days.

(21) Appl. No.: 15/310,604

(22) PCT Filed: May 12, 2015

(86) PCT No.: PCT/US2015/030439
§ 371 (c)(1),
(2) Date: Nov. 11, 2016

(87) PCT Pub. No.: WO2015/175578
PCT Pub. Date: Nov. 19, 2015

(65) Prior Publication Data
US 2017/0084163 A1 Mar. 23, 2017

Related U.S. Application Data

(60) Provisional application No. 61/991,830, filed on May 12, 2014.

(51) Int. Cl.
A61B 5/00 (2006.01)
A61N 1/39 (2006.01)
(Continued)

(52) U.S. Cl.
CPC .......... A61B 5/0006 (2013.01); A61B 5/746 (2013.01); A61B 50/13 (2016.02); A61H 31/005 (2013.01);
(Continued)

(58) Field of Classification Search
CPC ........... A61N 1/39044; A61N 1/36025; A61N 1/36014; A61N 1/046; A61N 1/37282;
(Continued)

(56) References Cited

U.S. PATENT DOCUMENTS 5,626,151 A 5/1997 Linden
6,073,046 A * 6/2000 Patel .................... A61B 5/0006
128/903

(Continued)

OTHER PUBLICATIONS

United States International PCT App. No. PCT/US15/30439 ISR/WO dated Aug. 18, 2015.

Primary Examiner — Paula J Stice

(57) ABSTRACT

A personalized acute care treatment kit is provided that includes components necessary for a lay caregiver to treat an acute cardiac event. The kit includes a medication box provided with medications selected according to the needs of the owner, a CPR device, a pacemaker, a defibrillator, monitoring and diagnostic devices and a computing device. The computing device is provided with a mobile application that captures patient data from the devices in the kit and automatically sends an alarm to a treatment professional when the patient data exceeds a predetermined threshold and establishes a communication link to with the treatment professional to allow the treatment professional to instruct the lay caregiver in using the contents of the kit to provide acute care.

9 Claims, 16 Drawing Sheets

(51) Int. Cl.
*G16H 50/20* (2018.01)
*A61H 31/00* (2006.01)
*A61M 16/06* (2006.01)
*A61M 16/00* (2006.01)
*G16H 10/60* (2018.01)
*G16H 20/10* (2018.01)
*G16H 40/67* (2018.01)
*G16H 70/20* (2018.01)
*A61B 50/13* (2016.01)
*A61J 1/16* (2006.01)
*G08B 21/18* (2006.01)
*G08B 25/10* (2006.01)
*A61B 5/0452* (2006.01)

(52) U.S. Cl.
CPC ............ *A61H 31/007* (2013.01); *A61J 1/165* (2013.01); *A61M 16/0051* (2013.01); *A61M 16/06* (2013.01); *A61N 1/3925* (2013.01); *A61N 1/3993* (2013.01); *G08B 21/182* (2013.01); *G08B 25/10* (2013.01); *G16H 10/60* (2018.01); *G16H 20/10* (2018.01); *G16H 40/67* (2018.01); *G16H 50/20* (2018.01); *G16H 70/20* (2018.01); *A61B 5/0452* (2013.01); *A61H 2201/0184* (2013.01); *A61H 2201/501* (2013.01); *A61H 2201/5043* (2013.01); *A61H 2201/5046* (2013.01); *A61H 2201/5097* (2013.01); *A61H 2230/04* (2013.01); *A61H 2230/207* (2013.01); *A61H 2230/30* (2013.01); *A61M 2202/0208* (2013.01); *A61M 2205/3553* (2013.01); *A61M 2205/3584* (2013.01); *A61M 2205/3592* (2013.01); *A61M 2205/505* (2013.01); *A61M 2205/52* (2013.01); *A61M 2205/584* (2013.01); *A61M 2209/06* (2013.01); *A61M 2230/04* (2013.01); *A61M 2230/201* (2013.01); *A61M 2230/205* (2013.01); *A61M 2230/30* (2013.01); *A61M 2230/62* (2013.01)

(58) Field of Classification Search
CPC .. A61N 1/37288; A61N 1/3904; G16H 10/60; G16H 50/30
See application file for complete search history.

(56) References Cited

U.S. PATENT DOCUMENTS

| | | | |
|---|---|---|---|
| RE40,365 E | 6/2008 | Kirchgeorg et al. | |
| 7,454,360 B2* | 11/2008 | Rosenfeld | G16H 70/20 705/3 |
| 7,774,060 B2 | 8/2010 | Westenskow et al. | |
| 2005/0015115 A1 | 1/2005 | Sullivan et al. | |
| 2005/0065445 A1 | 3/2005 | Arzbaecher et al. | |
| 2009/0076343 A1* | 3/2009 | James | A61B 5/0006 600/301 |
| 2009/0099469 A1 | 4/2009 | Flores | |
| 2011/0284004 A1 | 11/2011 | Silver et al. | |
| 2011/0298613 A1 | 12/2011 | Ayed | |
| 2014/0142963 A1* | 5/2014 | Hill | G16H 10/60 705/2 |

* cited by examiner

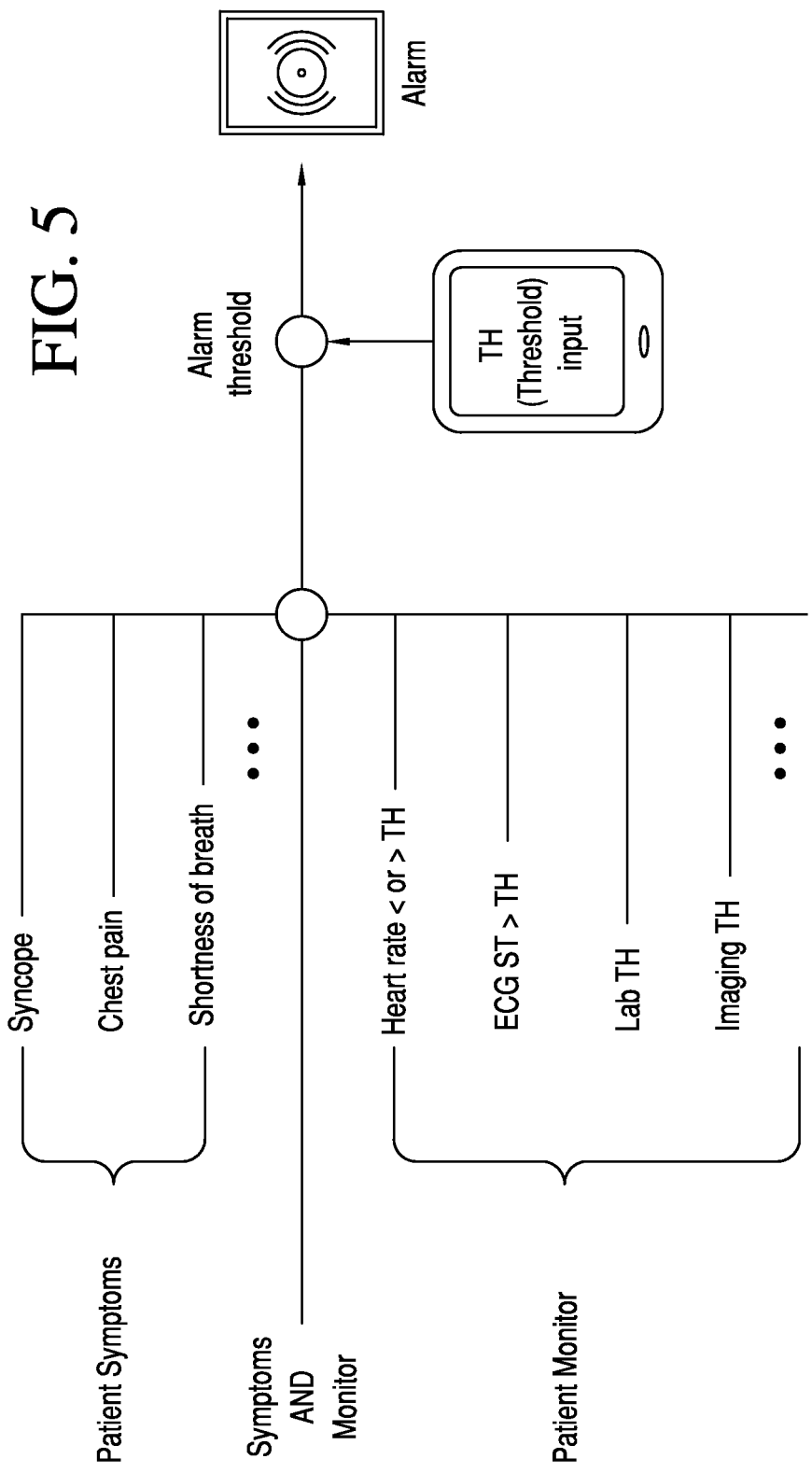

Locations of ECG Sensors

- RA — On the right arm, avoiding thick muscle.
- LA — In the same location where RA was placed, but on the left arm.
- RL — On the right lateral abdomen, similar to right leg
- LL — On left lateral abdomen, similar to left leg
- $V_1$ — In the fourth intercostal space (between ribs 4 and 5) just to the right of the sternum (breastbone).
- $V_2$ — In the fourth intercostal space (between ribs 4 and 5) just to the left of the sternum.
- $V_3$ — Between leads $V_2$ and $V_4$.
- $V_4$ — In the fifth intercostal space (between ribs 5 and 6) in the mid-clavicular line.
- $V_5$ — Horizontally even with $V_4$, in the left anterior axillary line.
- $V_6$ — Horizontally even with $V_4$ and $V_5$ in the midaxillary line.

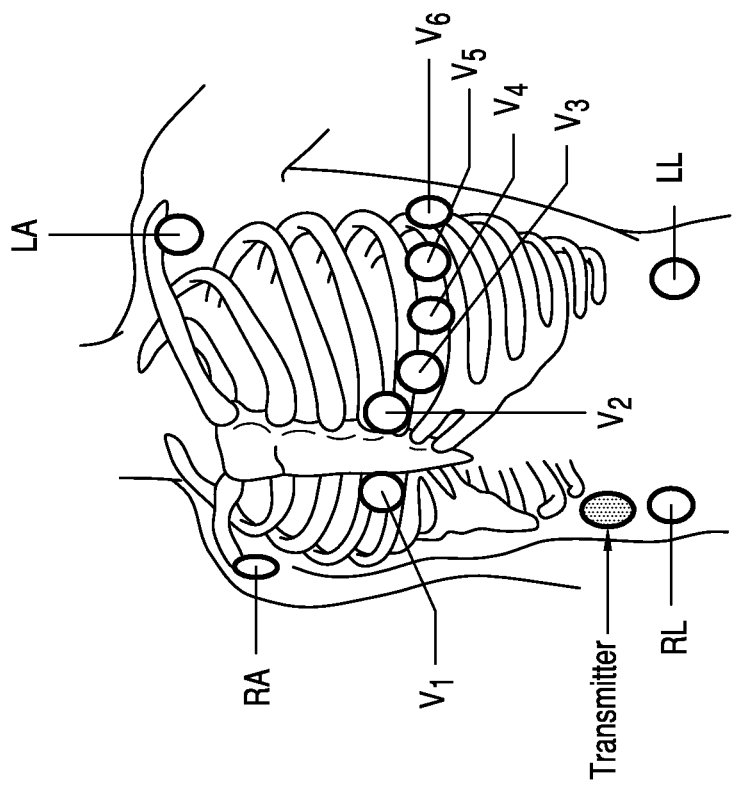

| Phase | | Contents | Guidelines |
|---|---|---|---|
| Pre-Event | Patient | Wishes, records, training | State Law Country Law International Law |
| | Provider | Consent, arbitration, communication channel and acute care process check up | |
| | Q/A | Monitor check, rehearsal management | Priority |
| Event | Acute care | Care conduction, diagnosis, treatment | Clinical Practice guidelines |
| | Recording & Tracking | Patient report, presentation, communication, transportation, etc | |
| | Monitoring | Measures of Vitals, ECG, Labs . . . | |
| Post-Event | Outcomes | Survival, complications, death | |
| | Records | EMR, CPR process | |
| | Performance | Accuracy and efficiency | |

FIG. 13

| | Virtual Guide | Process | Reference | Outcomes |
|---|---|---|---|---|
| Example | Implement ACC/AHA guidelines | Presentation: symptoms or signs | Universal Definition of AMI | Time to diagnosis<br>Time to treatment<br>Complication<br>Cost<br>Patient satisfaction |
| | | ECG: | | |
| | | Labs: Tpn, CPK/MB | | |
| | | Initial Tx: ASA | | |
| | | Transfer: Cardiac Hospital | | |
| | | Optimal Tx: PCI/Stent | | |

FIG. 14

| | Virtual Guide | Process | Reference | Outcomes |
|---|---|---|---|---|
| Sample | Implement ACC/AHA guidelines | Frequency distribution of symptoms and signs | AHA Guideline Subgroup analysis Diabetes patients | % Effectiveness<br>% Survival<br>% Mortality<br>% Morbidity<br>Efficiency distribution<br>Accuracy distribution<br>Cost distribution |
| #patients | | ECG change distribution | | |
| Age/Gender | | Labs results distribution | | |
| PMH/Meds | | Initial Tx distribution | | |
| Etiology | | Transfer distribution | | |
| Presentation | | Optimal Tx distribution | | |

FIG. 15

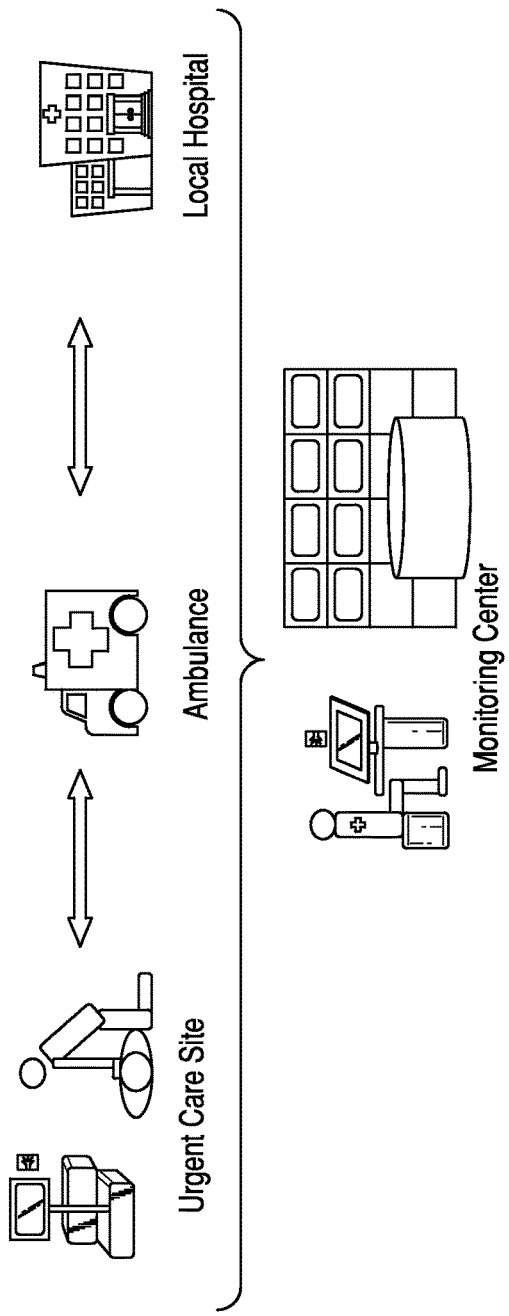

| Index | Index | Device | Algorithm/App | Function |
|---|---|---|---|---|
| Mt1 | Event Location | Tablet, smart phone, TV or PC | GPS | Identify patient location |
| Mt2 | Ambulance | Communication | Communication and instructions | Real time Communicate with hospital and patient |
| Mt3 | Doctor | Tablet/smart phone | Guidance and supervision | Care instruction |
| Mt4 | Hospital | Communication | Priority based onspecialty | Identify suitable service and prep for patient arrival |
| Mt5 | Family | Tablet/smart phone | Notification | Seek help and conduct care |
| Mt6 | Caregiver | Tablet/smart phone | Notification | Seek help and conduct care |
| Mt...n | | | | |

ACUTE CARE ECO SYSTEM INTEGRATING CUSTOMIZED DEVICES OF PERSONALIZED CARE WITH NETWORKED POPULATION BASED MANAGEMENT

I. CROSS REFERENCE TO RELATED APPLICATIONS

This application claims the benefit of U.S. Provisional Application No. 61/991,830 filed May 12, 2014 which is incorporated by reference in its entirety.

II. TECHNICAL FIELD

This invention generally relates to systems for the immediate or initial treatment of acute medical conditions and in particularly cardiac events. More specifically, this invention relates to systems and methods that direct treatment of cardiovascular events by non-specialty caregivers.

III. BACKGROUND

There are many challenges in current healthcare related to patients who experience acute events, especially patients experiencing acute heart attacks and cardiac arrest, making heart related death the No. 1 killer world-wide for the past 100 years. One such challenge is that there are no personalized medical devices selected and packaged for monitoring and care with individual patients anywhere at home, work or travel and anytime throughout fragmented care organizations, such as rehab hospitals, nursing homes, urgent care centers, physician offices, using a centralized care remotely with all related entities in the acute event Another challenge is that patient healthcare data is stored in silo systems from variety healthcare organizations, from hospitals, offices, nursing homes, etc. No electronic health record system integrate all care data for immediate access.

Still another challenge is that there are no real time monitoring with devices customized to individuals or facilities for organized and coordinate acute care Yet another challenge is that there are no standardized management eco systems to guide acute care based on national standard clinical practice guidelines and track outcomes for clinical and legal purposes.

IV. SUMMARY

In at least one embodiment, the present invention provides cardiovascular monitoring and treatment kit for a lay caregiver to treat a patient. The kit includes a case having a plurality of internal electrical outlets, a medication container disposed within said carrying case, an automatic external defibrillator disposed within said case, and an oxygen source disposed within said case. One or more sensors are provided that monitor cardiovascular parameters. A computing device is disposed within said case, the computing device includes a mobile application that receives cardiovascular parameters transmitted by the one or more sensors and generates an alarm when one or more of the cardiovascular parameters exceeds a predetermined threshold thereby indicating a cardiovascular event and transmits the alarm signal to preselected recipients.

V. BRIEF DESCRIPTION OF THE DRAWINGS

FIG. 5 depicts a decision tree for generating an alarm signal in accordance with the invention.

FIG. 6 depicts a diagram showing the appropriate location for ECG sensors.

FIG. 8

Figure 9:
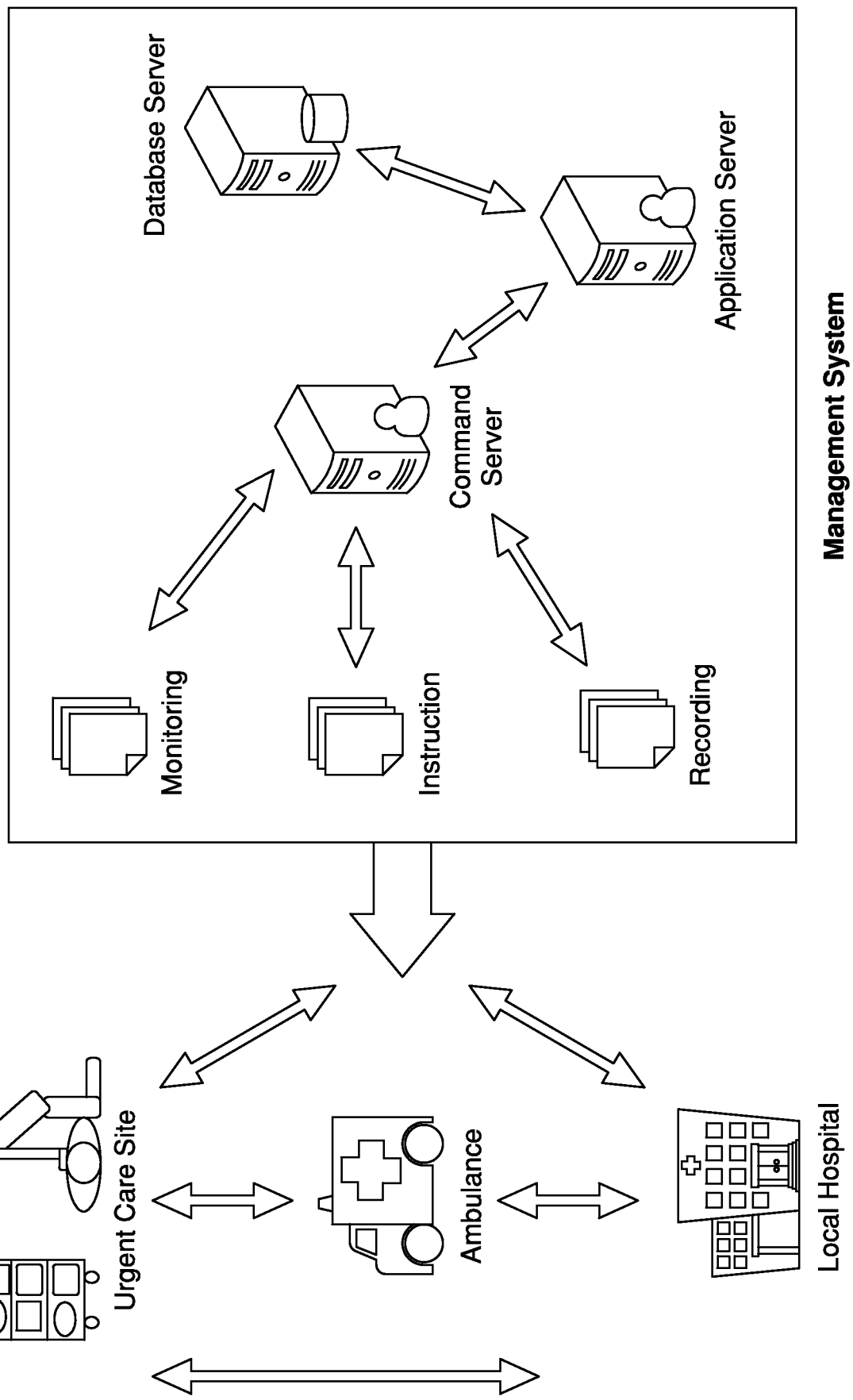

FIG. 9 A V-PRO Management Platform

Figure 10:
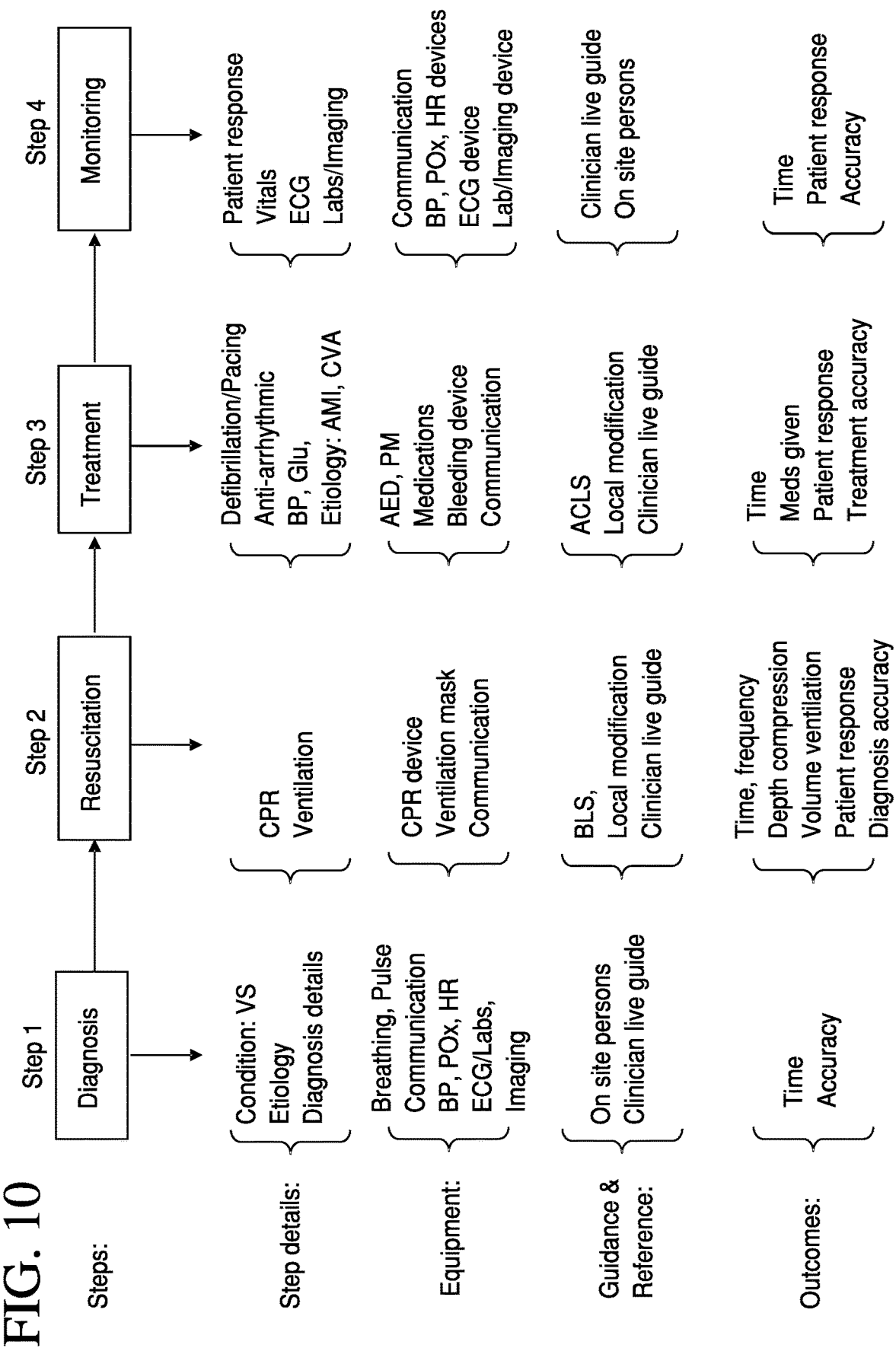

FIG. 10 The process module for acute event management

Figure 11:
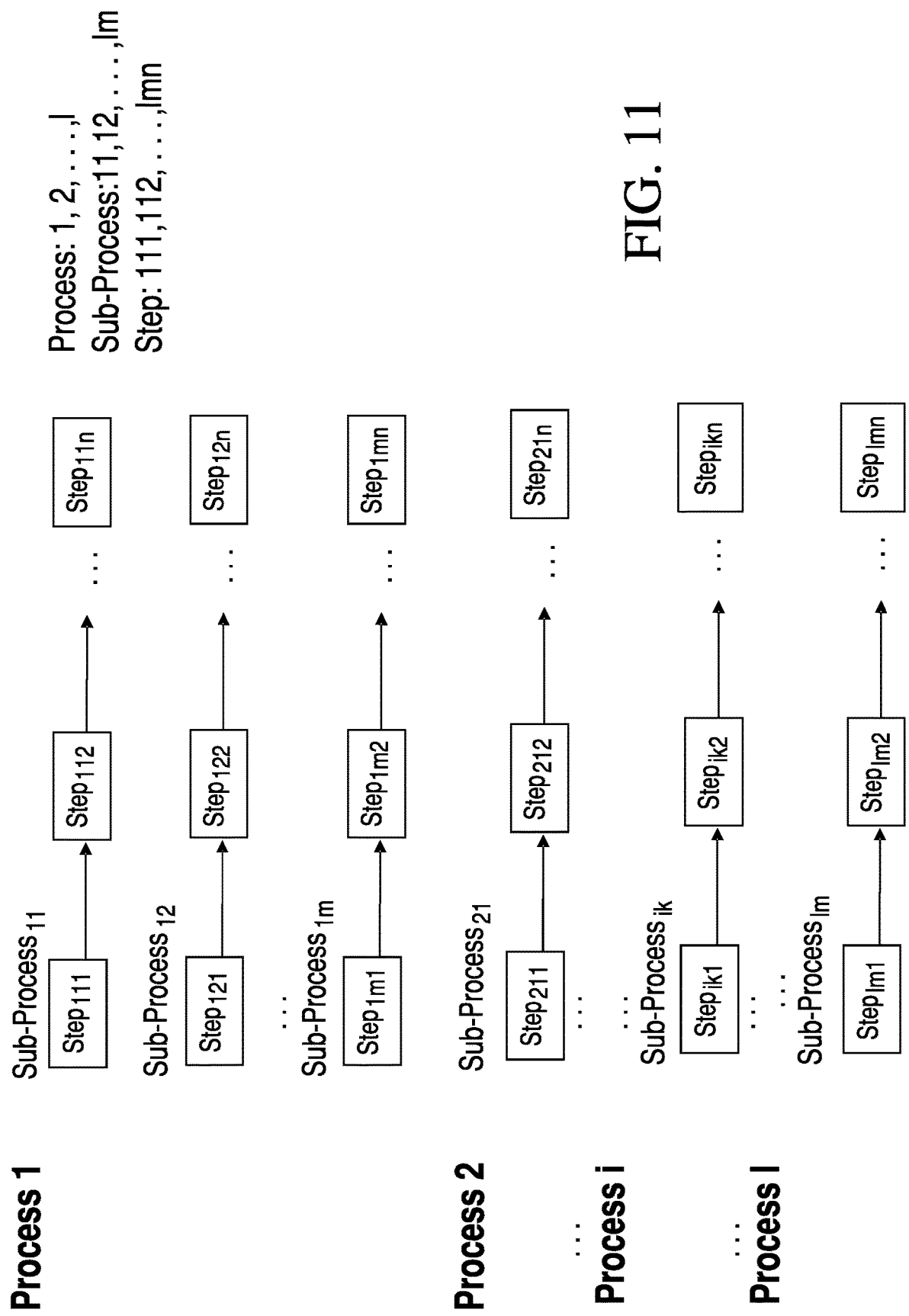

FIG. 11 Process Matrix

Figure 12:
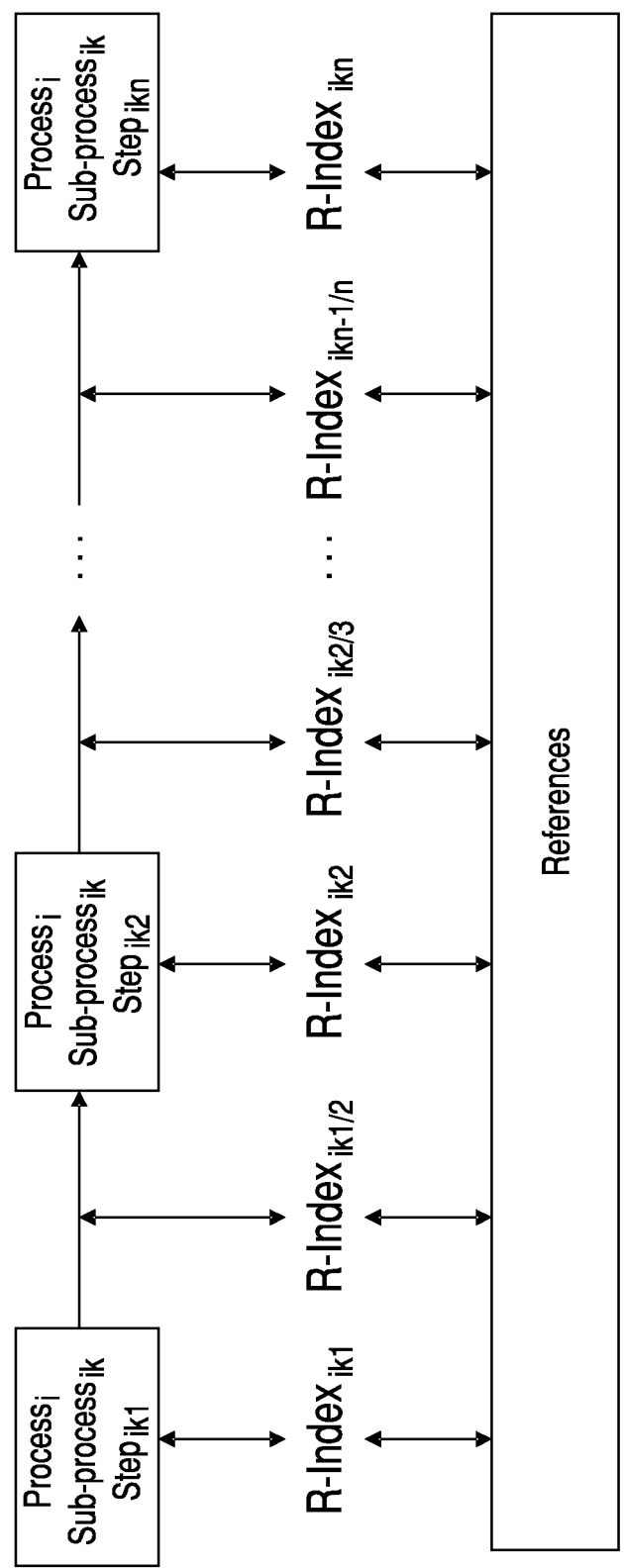

FIG. 12 Performance of the care process

FIG. 13 Acute Heart Attack at home depiction

FIG. 14-15 Echo System

Figure 16:
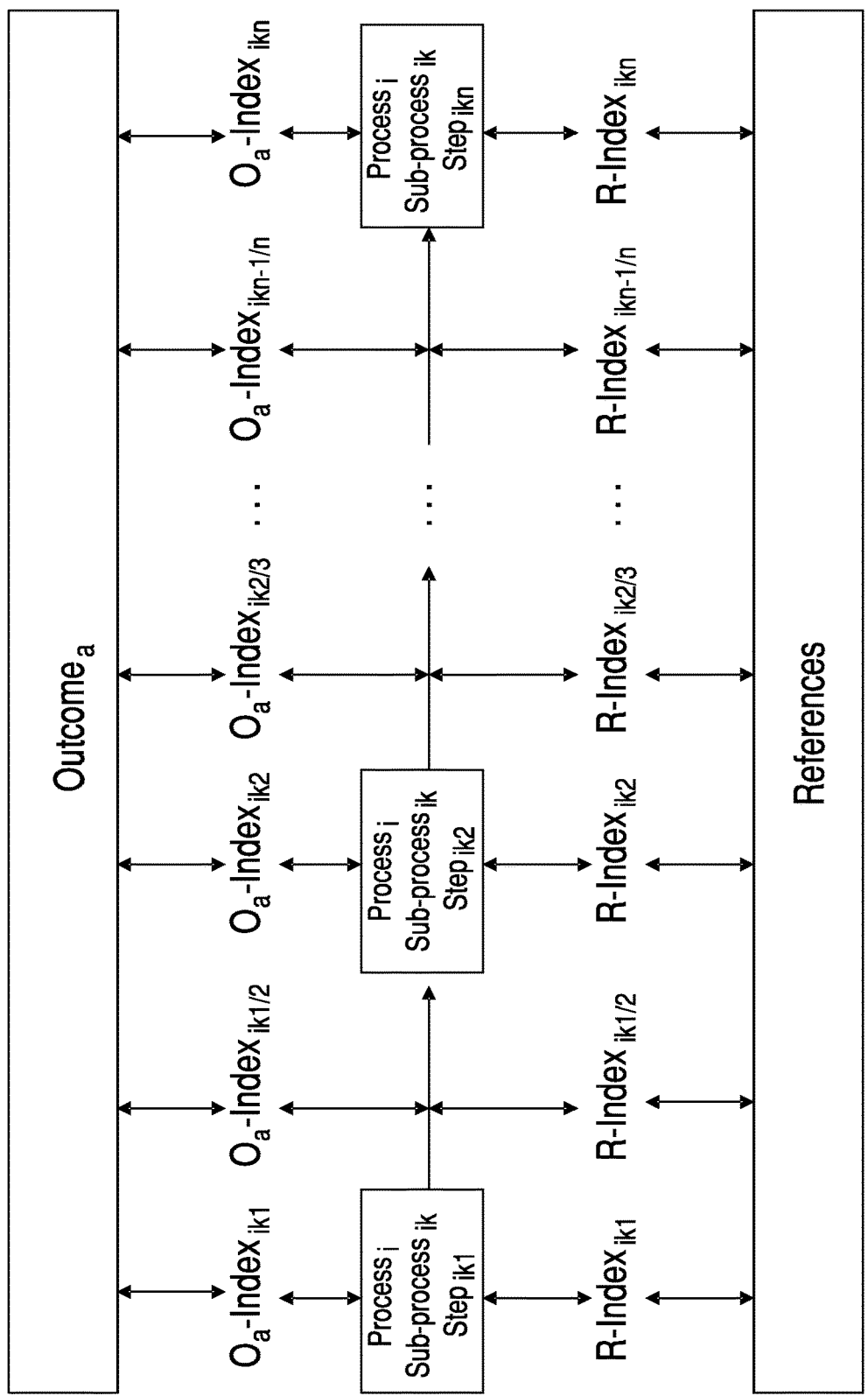
Figure 17:
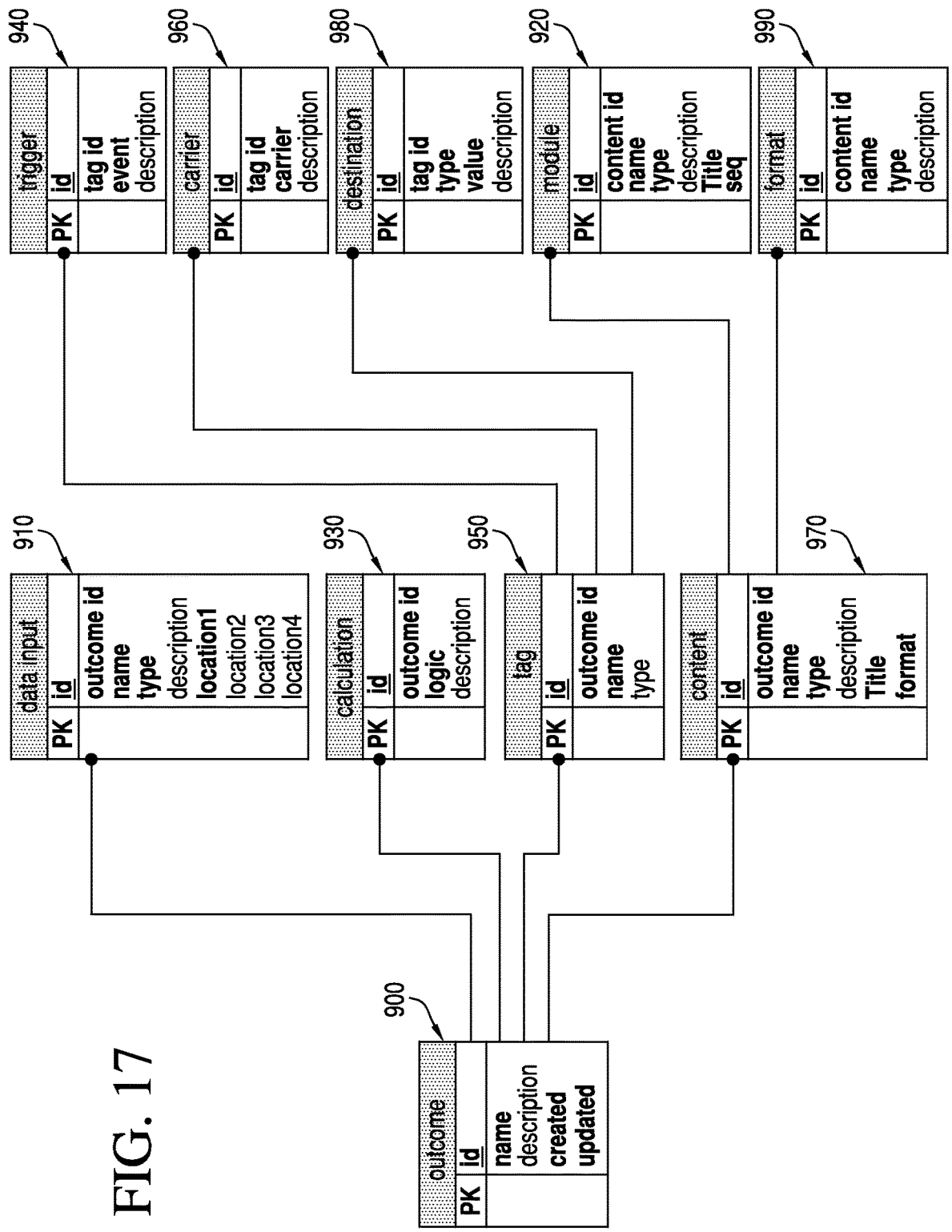

FIG. 16-17 Outcomes index

VI. DETAILED DESCRIPTION

The present invention provides an acute care eco system including personalized acute care treatment kits in combination with an acute care tracking system. The acute care treatment kits of the present invention are personalized for the individual patient and they are designed to assist a caregiver to administer acute care based on national standard clinical practice guidelines. The acute care tracking system tracks, documents and stores information relating to the treatment process.

Acute Care Treatment Kit

Figure 1:
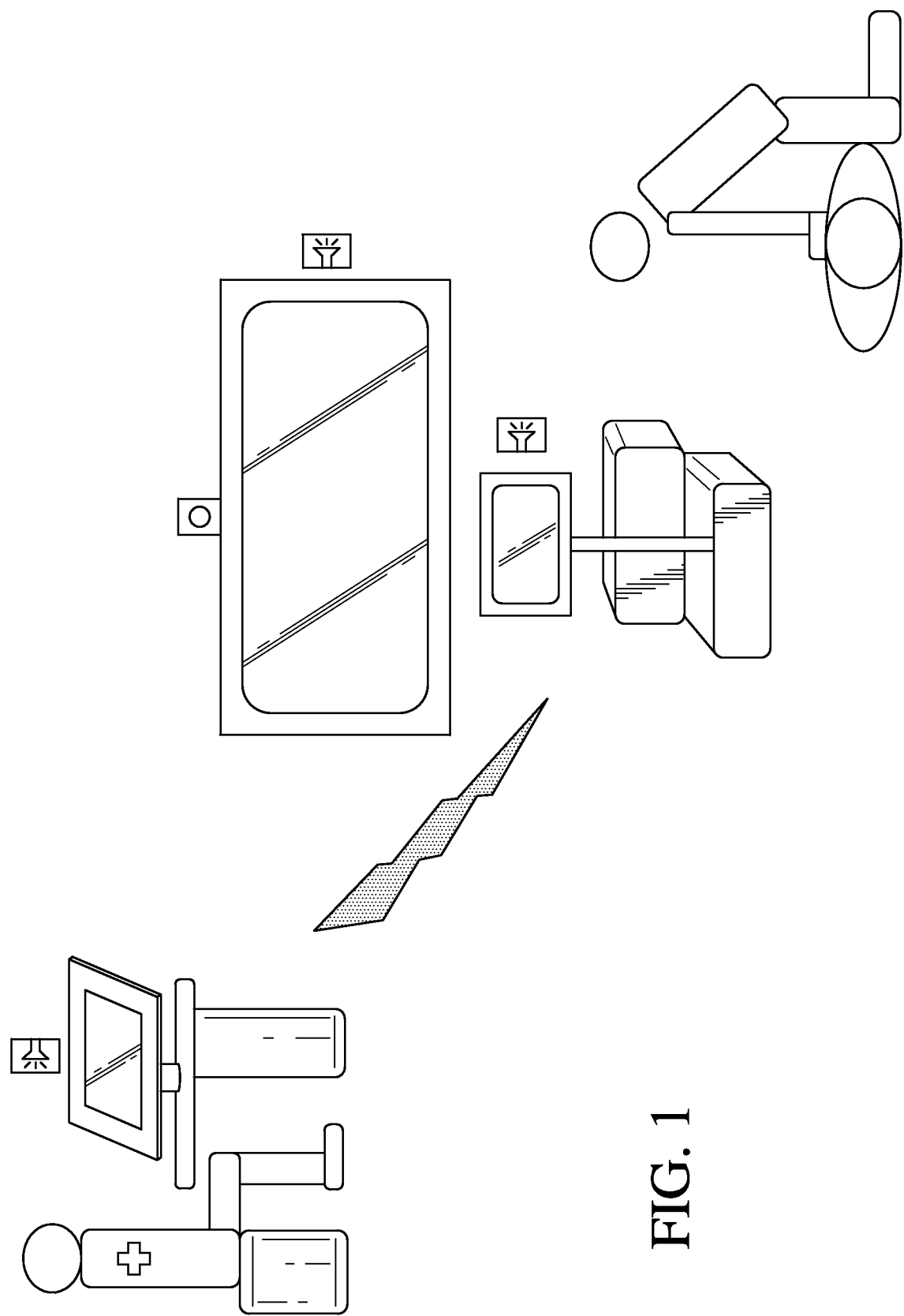
FIG. 1 illustrates an acute care treatment system in accordance with an embodiment of the invention.
Figure 2:
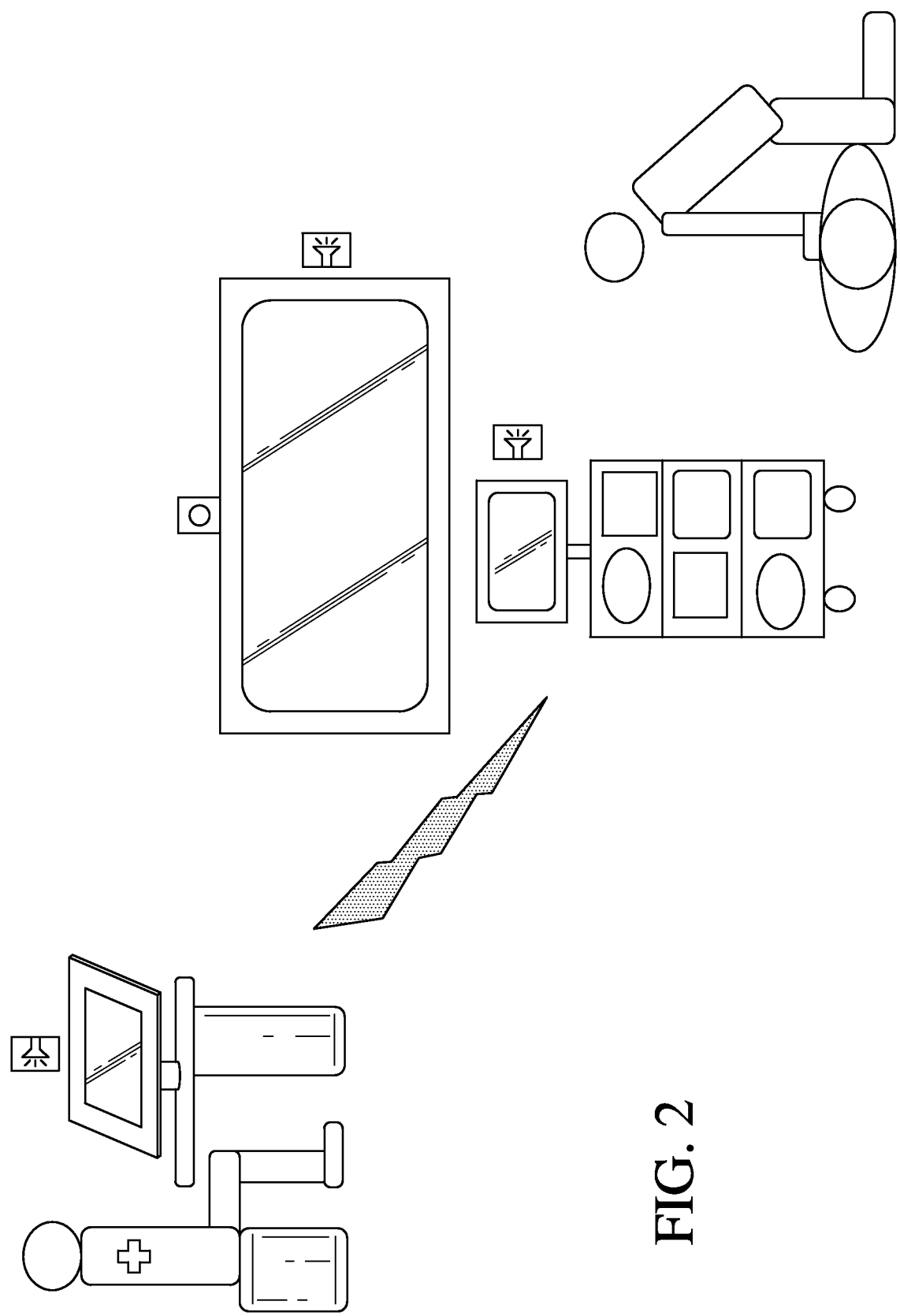
FIG. 2 illustrates an acute care treatment system in accordance with another embodiment of the invention.
Figure 3:
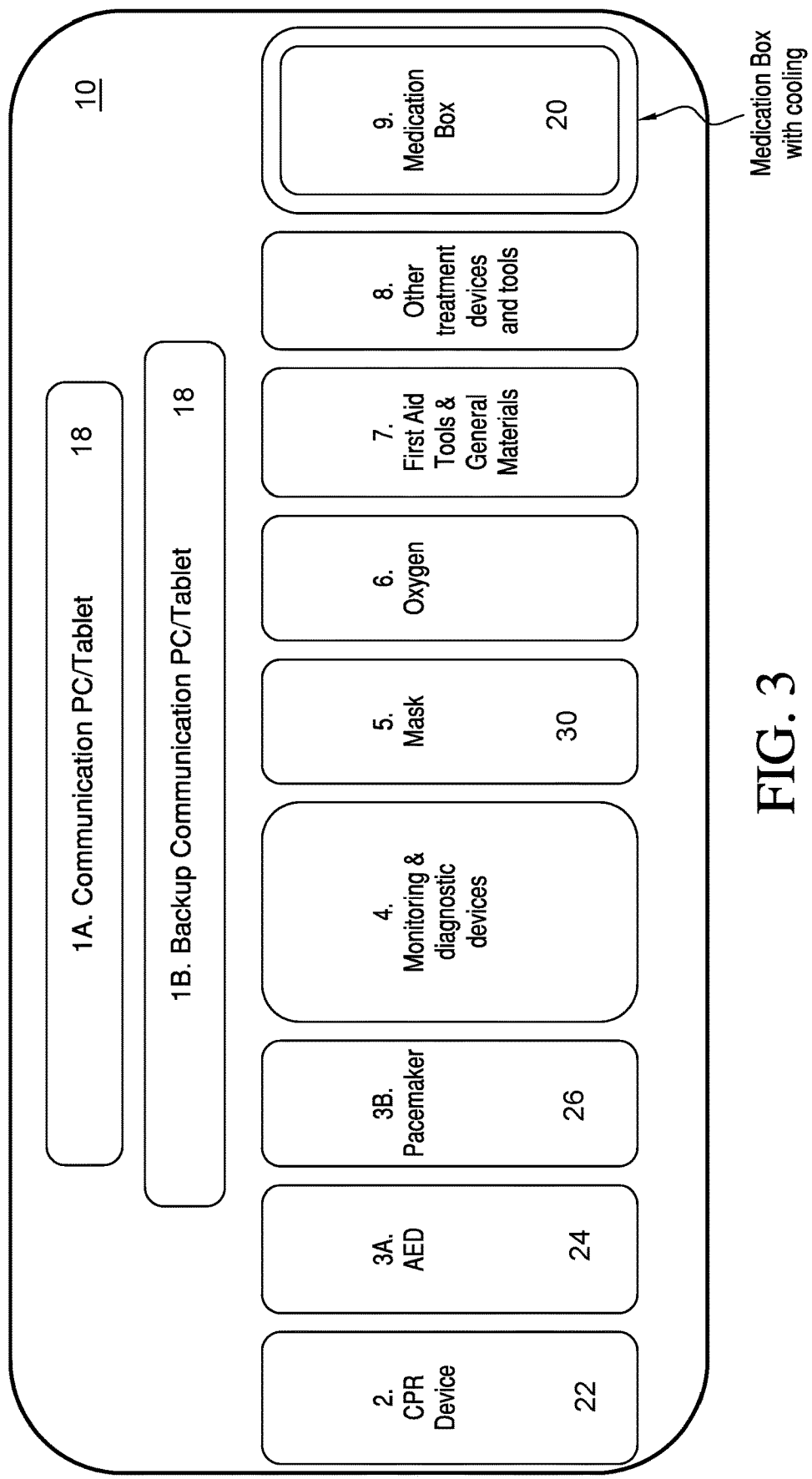
FIG. 3 illustrates an acute care kit in accordance with the invention.

In one embodiment of the invention, the acute care treatment kit is designed for detection and/or treatment of cardiac events and comprises a plurality of acute care devices $\{DV\}$, where $\{DV\}$: $\{DV_1, DV_2, \ldots, DV_n\}$, including diagnosis devices, intervention and treatment devices, communication devices and others disposed in an acute care case or arranged on a cart as shown in FIGS. 1 and 2, respectively. FIG. 3, depicts an exemplary embodiment of an acute care kit including an acute care case 10, e.g., a box, provided with a plurality of electrical outlets and including an internal power source, e.g., a battery and/or having a plug that may be connected to a wall outlet or an external power source. Acute care case 10 is preferably comprised of durable materials to help protect acute care devices 15 that are disposed therein.

In keeping with the invention, to assist the caregiver in using the acute care treatment kit, acute treatment case 10 includes one or more computing devices 18. Suitable computing devices include touch screen tablets such as iPAD, Android Tablet (for example Samsung Galaxy Tab), smart phones and personal computers provided with wide angle cameras (such as 180-360 degree camera). A lighting set may also be provided in acute care case 10 to improve the exposure of images transmitted via computing devices 18. Some embodiments include only a single computing device while other embodiments include multiple computing devices. Additional computing devices may allow multiple simultaneous communication channels, such as with the patient's family, a hospital, or additional guidance for resuscitation. For example, one computing device may be used for CPR or AED while a second computing device may be used to aid a second caregiver in administering medications. Computing devices 18 are preferably include wireless networking capabilities.

Figure 4:
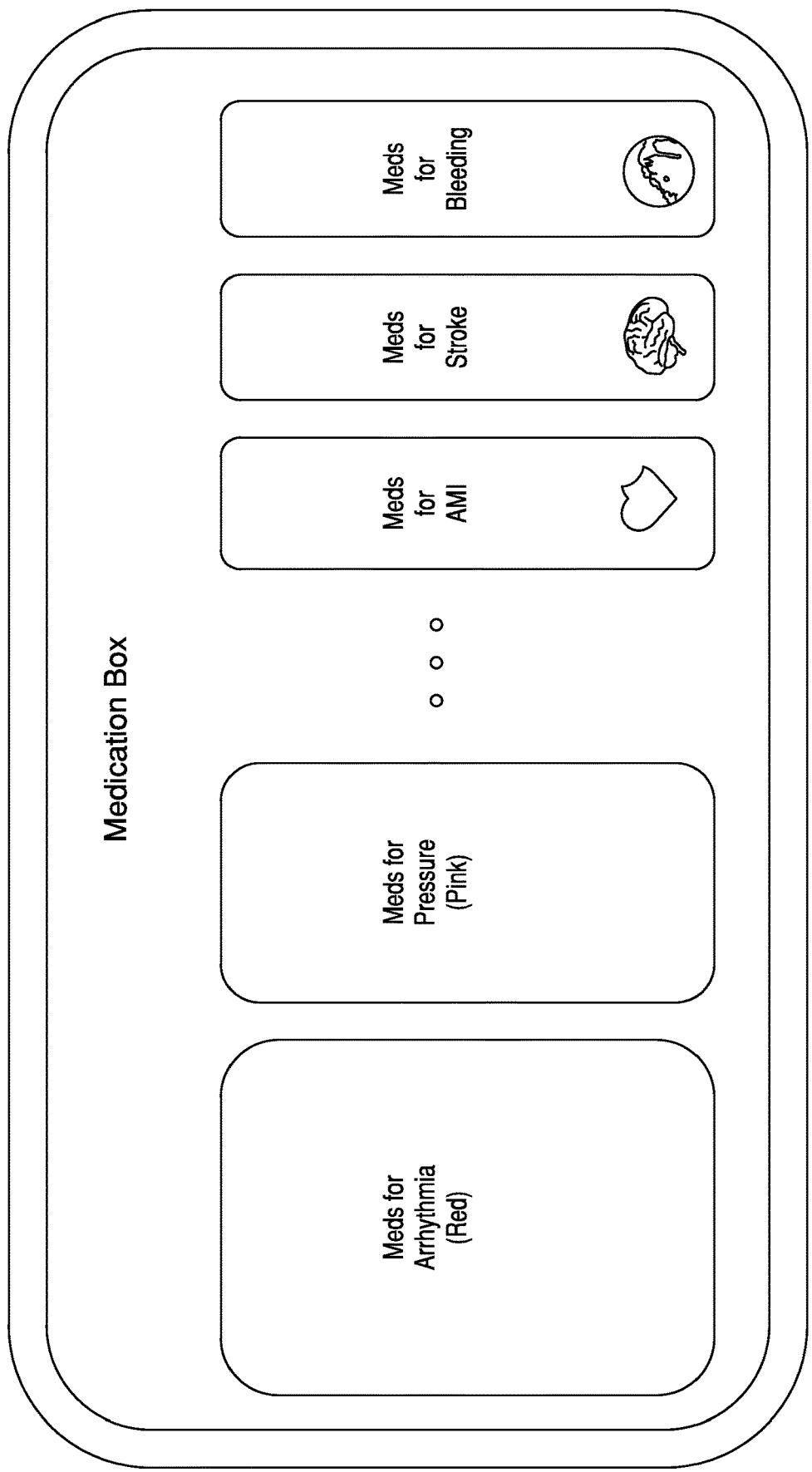
FIG. 4 illustrates a medication box of the acute care kit of FIG. 3.

Acute care case 10 further includes one or more medication boxes 20 containing a plurality of medications for patient treatment. In some embodiments, medication box 20 is refrigerated to permit storage of medications that must be kept at low temperatures. As illustrated in FIG. 4, the medications may be stored in compartments that are color coded, sequentially numbered and/or marked with special markers to be easily recognized by lay caregivers and easily referenced by treatment professionals. The medications to be included in medication box 20 may be selected according to the needs of the particular patient for whom the acute care treatment kit is designed as well as commercial considerations. In embodiments, medications are selected based on applicable practice guidelines for addressing cardiac events and the needs of the particular patient for whom the acute care treatment kit is designed. In some embodiments, medication box 20 may include medications for resuscitation, acute heart attack, acute stroke, acute bleeding, decrease or increase blood pressure, treatment of Bradycardia (low pulse), Tachycardia (high pulse), arrhythmias (such as atrial fibrillation, Asystole, ventricular tachycardia), common poison antidotes, allergies resulting from anaphylaxis shock, etc. Medication box 20 may include any combination of the foregoing medications. In at least one embodiment, computing device 18 tracks and stores the expiration dates of the medications stored in medication box 20 so that the caregiver can readily avoid administering a stale medication.

Referring back to FIG. 1, in some embodiments, acute care case 10 is further provided with a CPR (Cardiopulmonary resuscitation/chest compression) device 22, an automated external defibrillator (AED) 24, an external pace maker 26, ventilation mask 30, and oxygen 32. Acute case 10 is further provided with basic first aid devices such as needles and IV tubing and general materials such as gloves, clean sheets, and towels (not shown).

The acute care case 10 may include one or more sensors for detecting cardiovascular parameters selected based on specific patient needs. For example, in some embodiments, acute care case 10 may include an ECG monitor and ECG leads, particularly for a patient having ECG sensors, a blood pressure monitor, an oximeter, a CPR monitor, a device for checking glucose. Acute care case 10 may further include mobile lab kits such as rapid developed cartridges, similar to pregnancy test kits using urine, blood via finger sticks or even blood drawing with trained personnel, and small mobile imaging devices such as Echocardiography machines and small portable X-ray machines. The imaging devices may be more suitable for the acute care cart as they may not readily fit in acute care case 10. In some embodiments, one or more of the sensors, i.e., ECG monitor, the blood pressure monitor, the pulse oximeter, the glucose checking device include wireless data transmission capabilities allowing those devices to transmit data to independent devices.

Many lay caregivers may be unfamiliar with the specific locations of the chest to perform CPR and/or to inject cardiac medications. In keeping with the invention, acute care kit 10 may be provided with instructions, either in the form of a card or as part of module provided on computing device 18, for performing CPR including diagrams showing proper positioning for chest compression and/or the proper location for injecting cardiac medications.

To aid the user in using the acute care kit, acute case 10 may be provided with instruction card(s) including detailed instructions for using the devices included in the kit. In some embodiments, computing device 18 may include an interactive acute care instruction program including pre-recorded video/audio instructions for using the devices in acute case 10 and/or and for patient resuscitation. In some embodiments, the program may be voice activated and may be customized based on the needs of the patient. The acute care instruction program may be updated to reflect current resuscitation guidelines. When possible, it is preferable that the caregiver have real time communication with the treatment professional who is familiar with the patient so that the treatment professional can guide the caregiver's use of the acute care kit and immediate treatment of the patient.

Acute Care Mobile Application

To facilitate communication between the caregiver/patient and the treatment professional upon the occurrence of a cardiac event, computing device 18 is provided with an acute care mobile application for storing patient healthcare information data important for assessing cardiac events, that allows the caregiver or patient to send an alarm signal to a treatment professional, e.g., patient's personal physician or cardiologists. In keeping with the invention, in some embodiments, an alarm indicating the occurrence of an acute event may be triggered manually, e.g., by the caregiver placing a call to the treatment professional and/or by the caregiver activating a pre-programmed link in the acute care mobile application to send an alarm to a predetermined group of recipients including one or more of the patient's personal physician or cardiologist, a monitoring center, a clinic or nearby hospital with specialized cardiovascular care, friends and/or family members and/or work colleagues. CPR qualified persons can be registered and tracked in real time using known mobile phone technology. The alarm signal indicates that the patient is in distress and is in need of immediate attention. Upon receipt of such signal, the treatment professional may establish communication with the caregiver through computing device 18 or via a mobile phone or other communication device and provide the caregiver with instructions for using the acute care kit to treat the patient.

When the alarm signal is manually triggered, the treatment professional may communicate with either the caregiver or the patient herself to verify whether the patient is conscious. If the patient is unconscious, the treatment professional can activate emergency care, e.g., contact ambulance. The treatment professional will have the patient's geographic location due to the GPS function of the acute care app.

In other embodiments, the alarm signal may be triggered automatically by the acute care mobile application. The acute care mobile application is capable of receiving patient data from one or more of patient monitoring devices including but not limited to heart rate monitors, ECGs, imaging devices, pulse monitors, blood pressure monitors, oximiters, body position monitors, scales, stethescopes, etc. Patient data in the form of lab results (cardiac enzymes, electrolytes, etc.) and imaging data from the ECG is also provided to the acute care mobile application. In accordance with the invention, the acute care mobile application is provided with thresholds for patient data. Such thresholds may be based on practice guidelines or they may be determined by the treatment professional based on the patient's specific presentation.

The mobile application is further capable of receiving patient symptoms such as shortness of breath, chest pain, and syncope and is provided with thresholds for those symptoms. As illustrated in FIG. 5, the alarm signal may be generated when patient data exceeds predetermined thresholds and/or selected patient symptoms are present.

For example, in one embodiment, the alarm signal may be generated based on ECG data alone as ECG is one of the most important tools for diagnosing acute heart attacks. There are two type ECG sensors: invasive and non-invasive. Invasive ECG sensors can be implanted under the skin a small incision in the chest wall, but outside of chest cavity at locations such as shown in FIG. 6. These sensors are small in size and wireless with components of wireless batteries The wireless battery can be charged using wireless charger and connected to mobile device wirelessly to generate ECG waveforms for continuous recording, comparison and analysis (FIG. 1D. More details see in Section of Data Analysis). The ECG wave signal diagrams are in pdf or other format and the may be captured by the acute care mobile application.

Non-invasive ECG sensors include sensors that are adhered to the patient's skin at standard locations and hand held ECG's such as SmartHeart™ available from SHL Telemedicine. The ECG wave signals generated by these non-invasive devices may also by captured by the acute care mobile application.

Figure 7:
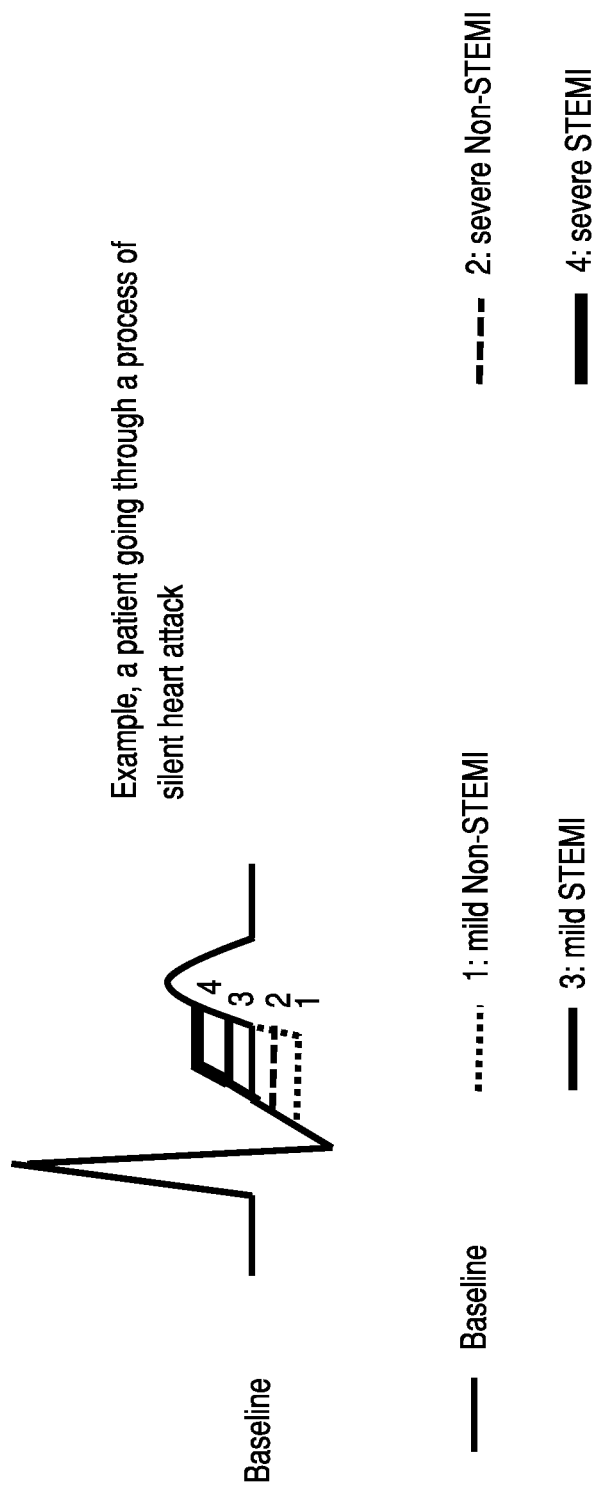
FIG. 7 illustrates ECG changes over time of a patient experiencing a silent heart attack.

ECG monitors can continuously record and monitor ECG waves for acute cardiovascular events such as acute myocardial infarction (AMI), arrhythmia or stroke and the acute care mobile application can continuously analyze the ECG data as illustrated in FIG. 7. Note that STEMI in FIG. 7 refers to ST Elevation Myocardial Infarction. In keeping with the invention, acute care mobile application may be programmed with a predetermined threshold specific to the patient set by the patient's physician or cardiologist. For example, for a patient with cardiomyopathy (weakness of pumping function and heart failure), the physician can setup an alarm trigged at pulse rate at 60 beat/min; whereas a normal person's pulse rate can be preset at 40 beat/min. When the pulse rate is lower than the threshold, the acute care mobile application generates an alarm signal and automatically sends that signal to the patient's predetermined network. The alarm signal includes a message with the specific location of the patient and a statement that the patient requires immediate assistance.

In some embodiments, the patient may be provided with various additional sensors including pulse sensors, blood pressure sensors, and pulse oximeters. The sensors may be implanted or they may be connected to the patient's wrist, chest, arms or fingers depending upon the nature of the device. The sensors transmit data which may be captured by the acute care mobile application with such data to be compared against thresholds set similar to the ECG sensors.

Legal Aspects:

Telemedicine shall increase legal activities, especially remote care involved extra layer and complexities of technologies, communications and care processes, more room for errors. This invention has specifically designed an automated process, method and apparatus to optimize legal protection for all parties, patients, lay person in the acute care and providers as shown in FIG. 8.

A. Monitors and Care Functional Level and Accuracy

The App operating the devices will check with the function of medical devices, care updates (such as care standard changes, new monitor added to the market, the use of monitor priorities and indications for certain diseases, etc) periodically (daily, weekly or as needed) for synchronization and calibrations using established calibration techniques or physically checked/compared with other standard devices. If the device functional accuracy is out of the range defined by the manufacture, a request will be send to both manufacture and monitoring center for adjustment, rapier or replacement.

B. Communication Functional Level and Accuracy

The App operating the devices will check with the function of communication devices periodically (daily, weekly or as needed) for synchronization and adjustment using established communication techniques or physically checked using industry standards. If the device functional accuracy is out of the range defined by the manufacture, a request will be send to both manufacture and monitoring center for adjustment, rapier or replacement.

C. Clinical Guidelines and Standards

The App guiding the care will check with the function of care and medication updates (such as care standard changes, Clinical Practice Guidelines on disease diagnosis and treatment, each steps are implemented as guideline recommended, new medication on the market, medication use priorities and selections as well as expiration date, etc) periodically (daily, weekly or as needed) for synchronization and comparison with clinical practice standards. If the care guidance is out of the range defined by the guidelines, a version update will be downloadable to the user's APP.

D. Process and Steps of Healthcare Provider Instructions

The App for the process of healthcare providers from remote location will check with the function of instruction and operation updates (such as acute operation standard changes, new location of the hospitals near the patient event site, the service expertise selections as well as service availabilities at the time of the event based on the physician schedules, etc) periodically (daily, weekly or as needed) for synchronization and comparison with local care and care operations. If it is outdates, a version update will be downloadable to the user's APP.

E. Operation Instruction of an Lay Person for the Onsite Acute Care

The App for the operation instruction process of a lay person care provider will check with the function of instruction and operation updates (such as acute operation standard changes, the language and graphic updates on the instructions, the instructions on new devices, operation and communication, etc) periodically (daily, weekly or as needed) for synchronization and comparison. If it is outdates, a version update will be downloadable to the user's APP.

F. Automated Selections of Laws and Guidelines Based on Geographic Locations

The App for the law selection will check with the location of the event, the patient's prior arrangement, lawful permission, restrictions and prohibition to each steps of the process in the acute care, etc periodically (daily, weekly or as needed) for synchronization and update. If it is outdates, a version update will be downloadable to the user's APP.

G. Documentations Tracking the Process of the Acute Event

Patient consent on entire process. Prior determination of all related contents in terms of his/her info access, communication to physician selections, what can or cannot be done in the acute event or critical illness. If needed arbitration and certain level of agreement will be signed, especially for physician protections.

H. Event tracking:

Detailed recording (voice and video) of the process, communications, decision makings and results of each steps during the acute event is provided.

Analysis

Analysis is provided of provider conduct or performance: communication on diagnosis, treatment, triaging and transfer, survival and complication. For complicated patients with severe diseases, patients and family are well informed and each steps of plan are signed by the patient and family.

Documentation: based on 1-5 Consent and arbitration agreement are cleared outlined telemedicine procedures and risks.

Data Collection and Storage

In accordance with an aspect of the invention, healthcare data is collected from the devices contained in acute care kit 10. This data is digitized and stored in one or more databases for analysis.

Various indexed data items {ID} are collected from devices {DV}.

Indexed data items (or Index) {ID}: {$ID_1, ID_2, \ldots, ID_{n1}$}
An index $ID_i$ may contain 1 or multiple sub index.

$ID_i = \{SID_{i1}, SID_{i2}, \ldots, SID_{im2}\} \in \{SID\}$ where: subindex{SID}: {$SID_1, SID_2, \ldots, SID_{n2}$}

To improve acute care, it is important for treatment professional to analyze each and every aspect of an acute care event. Accordingly, in accordance with the invention the following is captured and recorded using computing device 18:

A Record the whole process from the initial activation to hospital

B All images and communications of resuscitation process:

C All measures (BP, HR, ECG, Pox, Glucose), Labs and related imaging

D All treatments:
CPR and ventilation
AED or PM
Medications
Equipment

E All communication with patient family and hospital/ambulance group

F Served as "Black Cart" that cannot be altered or erased

Data Collections: Acute

| Items/Index | Contents |
| --- | --- |
| 1. Clinical Info | |
| Clinical History | Diagnosis |
| Current stage | Active problems, such as heart failure |
| Medication | Allergies and current medications and changes |
| Labs | Recent labs |
| Live measurement | Physiological |
| Acute Event Diagnosis | Diagnosis based on ICD9 or ICD10 |
| Acute Event Treatment | Based on treatment options and recommendations from Guidelines |
| 2. Transportation | |
| Current location | Transportation means: speed and safety |
| 3. Tertiary Care | |
| Hospital specialty | Availability |
| Outcome rankings | Care outcomes and comparisons |

| | Previous | Current | Now: |
| --- | --- | --- | --- |
| Diagnosis | CAD | AMI | Unstable |
| Measurement | | | |
| Arrhythmia: | Normal | Non-sustained VT | |
| Blood pressure | 140/80 | 170/100 | |
| ECG | Normal | ST Elevation | |
| Medications | Lisinopril 20 mg | Lisinopril 20 mg | Metoprolol 25 mg PO NTG SL |
| | ASA 81 mg | ASA 81 mg | ASA 325 mg QD Plavix 75 mg QD |

After each acquisition, the acute care mobile application sends all indexed data {ID} to a database server in real time, (such as measure blood pressure) or simultaneously with recordings in real-time (such as the invasive ECG). The new incoming data will be compared with prior data of the same categories to detect any changes. If there are changes a physician/on-call provider will be notified immediately for appropriate treatment if necessary, e.g., in case of arrhythmia or acute heart attack.

Database server stores all data collected or used in this application. In some embodiments, multiple database servers may be used for data replication and to increase the availability of system resources. Suitable database servers include Microsoft SQL Server version 2008 and forward and Oracle Database Server: version 9 and forward. In some embodiments, the data base server is used for all functional databases of the system.

V-PRO: An Eco System for Acute Event Analysis from Individual to Group

A V-PRO Management Platform according to the invention is shown in general block-diagram form in FIG. 9. The PRO outcome management system generally comprises a standard client-server architecture including an application server, a database server, web or network server and one or more hospital service provider and/or ambulance computers/servers. Application server operates a suite of functional modules including process module, outcome module and reference module. In one embodiment, hospital service provider/ambulance computers are connected to application server, database server and web server via the Internet or secured wireless network. However, these computers may be connected in any available network architecture. Application server, database server and web server may be resident on a single computer or may be distributed between multiple computers. Web server provides a convenient way for authorized users to access system. Using web browsers, users may quick identify emergency care guidelines, patient's medical records, and patient own healthcare contacts. Web server generates graphic user interfaces which enable various kinds of web services for end users (doctors, directors, etc.). Using the servers, the detailed Process Module, Reference Module and Outcome Module will be created. An interface system is used to link the servers to map the data sources for data transfer.

Webserver may be implemented on various computer platforms. Windows® platforms and Linux® platforms are suitable. For Windows, many versions of operating systems can be used, such as Windows 7 Server, Window 8 and the like. For Linux, Red Hat v.12.04 and later are suitable operating systems. Suitable web server software includes Apache servers and Tomcat servers. Database server stores all system data. In some embodiments, multiple database servers may be used for data replication and to increase the availability of system resources. Suitable database servers include Microsoft SQL Server version 2008 and forward and Oracle Database Server: version 9 and forward. In some embodiments, the data base server is used for all functional databases of the system. Application server creates a middle layer between web server and database server. Users submit their requests to web server which passes those requests to application server. Application server verifies and analyzes those requests and retrieves data from database server when needed. Application server implements guidelines, logics and algorithms. Application server may be implemented on a variety of computer platforms. Suitable operating systems include Windows operating systems such as Windows 7 Server, Windows 8 Server, and Linux operating systems such as Red Hat v.12.04 and forward. Suitable code compiling software such as PHP, Java, .Net and others Modules The V-PRO Management Platform contains four big modules: Virtual Guidance, Process, Reference, and Outcome.

In every processes {PR}, we evaluate outcomes {OC} considering indexed data {ID} from devices {DV}, guidelines {GL}, and responses {RS}.

{OC}=Function ({PR}, {DV}, {ID}, {GL}, {RS})
  where: {OC}: Outcomes
    {PR}: Processes
    {DV}: Devices
    {ID}: Indexed Data
    {GL}: Guidelines
    {RS}: Responses 2) Virtual Guidance: Initial Guidance Guidelines for resuscitation or critical care for patients in acute events, such as cardiac arrest, acute heart attack, stroke, etc., will be provided at the point of care, either at patient home, office, travel, or even at hospital, will be provided immediately for standard immediate care to compliance to quality of care and decrease legal risk of deviation of standard care.

3) Process: Specific Steps of the Acute Event Management

The process module for acute event management (FIG. 10 and FIG. 11) includes a multiple-tier structured matrix, as illustrated in FIGS. 10 and 11: multiple steps form a sub-process, and multiple sub-processes form a process. Multiple processes are ordered from basic ones to the top, usually used to describe functions of the entire healthcare service structure and delivery. The multiple processes can include an administrative hierarchy (such as hospital, county, state, country) or functional hierarchy. At the end, the matrix of the processes provides a map of structure with sequences and layers of sub-processes/steps. The processes and their sub-processes of the acute event management are shown in the table? The hierarchy and relationship of the sub-processes and its steps provide functions for an Acute Event Management process.

Processes {PR}: {$PR_1$, $PR_2$, ..., $PR_{n4}$}
$PR_j$={$ST_{j1}$, $ST_{j2}$, ..., $ST_{ji}$}∈{ST}
where: Steps {ST}: {$ST_1$, $ST_2$, ..., $ST_{n5}$}

TABLE

| Processes of Acute event management | | | | |
|---|---|---|---|---|
| | Process 1: AMI | Process 2: CVA | ... | Process N |
| Sub-Process 1 | STEMI | Embolic (dislodge a clot) | ... | ... |
| Sub-Process 2 | Non-STEMI | Stenotic (blockage of an artery) | ... | ... |
| ... | ... | ... | ... | ... |

As shown in FIG. 11, indexes are created based on the processes with corresponding sub-process and steps. The indexes are used to link related references and outcomes to the process matrix (FIG. 11) for performance assessment.

Process: A process includes: (a). multiple sub-processes each having multiple steps, and (b). providers involved in the process. The process is also linked with the references (as a standard or guidelines) related with the steps of the process and the outcomes of the process. A process can be modeled using the system of this invention in accordance with the following procedure:

A. Identify and define the sub-processes included in the process. In the example illustrated in FIG. 10, the sub-processes are on site of acute event, Ambulance/transportation and Hospital/Specialty Care.

B. Identify and define each step of a sub-process. As illustrated in FIG. 6, each sub-process includes multiple steps. A typical sub-process of acute event management includes the following four steps:

Registration: In this step, a patient is registered at the front desk. Patient # and insurance information are input into this application. Patient Info, Service specialty, Visit classification.

Data Collection: This step is finished by a registered nurse or assistant. This step is started by Step 1 review. This application collects detailed data items about Past medical history, Risk factors, Related test results, medications.

Define Problems: A medical doctor or clinician works on this step. It begins with Step 2 review. This step involves Presentations, Physical Exam, patient conditions, and indications.

Decision-making: This is the last step of this sub-process. It is also done by a medical doctor or clinician. Step 3 results will be reviewed. and healthcare orders, including initial order, reference order and final order, should be done in this step.

C. Identify and define the data resource or input source for each step. The data sources for data needed to perform each step will be mapped from the related data extracted from the emergency care recordings.

D. Identify and define players involved in each step. The provider responsible for performing the step is identified by identifying characteristics such as name, position, employer, etc.

E. Identify and define related references for each step. The References by definition relate to various steps of the emergency care process. All references that relate to a given step are identified and indexed to their corresponding steps, sub-processes and process as shown in FIG. 8.

F. Identify and define the outcomes related with the process. Based on the purpose of the analysis as defined by the user, the user names and selects the related outcomes for the care process.

Process module collects data from each step of the patient care process, maps the data and stores the data in one or more indexed databases to provide the overall function of the Process module as illustrated in FIGS. 10 and 11.

4) Reference (Guidelines or Standards): Guidance Tune-Up, Customized

References are input to Reference module from standards or guidelines, indexed to the related processes, sub-processes and steps, and stored into a reference database.

Guidelines {GL}: {$GL_1$, $GL_2$, ..., $GL_{n6}$}

Reference module also analyzes one or more sub-processes or steps of the emergency care process in comparison with the references to generate an emergency care process performance indicator. More particularly, the indexed references are compared to related indexed, steps, sub-processes and processes to evaluate the performance of the care process. FIG. 12.

5) Outcomes: Tracking Results Based on Variety of Outcomes, Such as:
   a. Stabilized or Unstable:
   b. Admission/Readmissions
   c. Complications/Death Outcome module provides systematic follow-up to emergency care processes as various kinds of outcomes. A user can select or define its own outcomes and outcome module, then, tracks and analyzes those outcomes. In accordance with an embodiment of the invention, many exemplary categories of healthcare outcomes are described. However, a user may define other new outcomes. Outcomes are the results and final judgment of the performance for both patient care selection Process and the References. There are many different outcomes in the healthcare field. Exemplary outcomes addressed herein include clinical, financial, administrative, etc.

The VPRO system above illustrates how a patient going through the acute event, for example, a patient having acute heart attack (AMI: Acute Myocardial Infarction) at home as depicted in FIG. 13.

Virtual guide: the patient care initiated under virtual guidance using his personalized devices for diagnosis, communicated with his physician or acute care provider network for treatment, transportation to a high performance hospital nearby and conduction of the entire care of the acute event.

Process: The specific process for AMI, reporting symptoms, ECG monitor and interpretations, with labs if available, treatment of Aspirin or medications, etc Reference: The process is managed under the guidelines of American Heart Association for AMI, implemented via the System Outcomes: The results of the AMI event care include the clinical outcomes (the degree/size of MI, complications, success of save using medications or procedures (such as stent), as well as the care implementation in accuracy, efficiency executed by the care givers (family, friends or lay persons) with the patients at the time of the event, etc.

6) Population Performance: Group VPRO

The Population VPRO is to assess the performance of acute care for a group of individuals from each of their VPRO data (patients: such as diabetes, male, 50-60 years old; care giver: such as healthcare professional, lay person after training for the system, or lay persons without training; providers: such as primary care vs specialists, patient personal physician vs service network, etc.), a location (such as at home, a city, a state, a country) or a service system (such as ACO group, homecare, insurance, etc).

The focus of the Eco System is automatically to collect all patients in similar conditions, to analyze the performance (for example, accuracy and efficiency) of the process or acute event care and to improve outcomes (such as clinical, financial, etc) as depicted in FIG. 14.

Through the analysis using the Eco System, one may identify the gaps of the process and modify it for a better care.

Through the analysis using the Eco System, one may also identify the gaps of the Guidelines and modify it for a better care. For example, if a diabetic patient with potential AMI, in additional to ECG, a lab for glucose and potassium need to be checked also, since very high potassium level can cause ECG changes, mimic AMI. And the treatment can be very different: for real AMI, need to give clot buster (such as tPA) and for hyperkalemia and hyperglycemia, one must give meds to decrease potassium and glucose (such as insulin).

The whole purpose of improvement of Process and Reference is based on prior outcomes and for better future outcomes Education, Training and Practice Process:

It is important to train patients with the kits and lay persons who related with the patient and may perform the device and acute care on the patient. The process includes the following:

1). Selection of the Kits: Based on a patient's clinical condition and potential life threatening acute event, a specific set of device kits is selected in a package of box, bag or even cart for a large group of people, such as a company's building.

2). Training on the kit use. All selected devices use, training of basic life support (BLS) and even advance cardiovascular life support (ACLS) will be provided and even required to some personnel with certification to operate the devices or acute care in a standard manner.

3). Rehearsal under remote monitoring and instruction automated scheduled. Since most lay persons do not operate the acute care in a regular interval as healthcare providers, scheduled rehearsals. And this training is automatically scheduled and checked to assure the quality.

4). Performance evaluation. The rehearsals repeated in a regular intervals are evaluated and scored by health professionals for performance assessment. If any lay person cannot reach an optimal care to operate the devices, additional training or frequent rehearsals need to be repeated and reassessed.

The invention claimed is:

1. A method of diagnosing, monitoring and treating cardiovascular or pulmonary events using an acute care kit provided with a computing device, resuscitation devices, acute condition medications, mobile lab kits or mobile imaging devices, said method comprising:
   receiving cardiopulmonary parameters of a patient from (i) one or more subcutaneously embedded sensors including at least an invasive 12-lead ECG or (ii) one or more surface diagnostic hospital grade devices including at least a non-invasive 12-lead ECG;
   receiving lab or imaging results;
   generating an alarm signal when one or more of the cardiovascular parameters exceeds a predetermined threshold, the alarm signal being further based on the lab or imaging results and the alarm signal indicating a cardiovascular or pulmonary event;
   transmitting the alarm signal to a network including a remote treatment professional designated to provide immediate treatment for the cardiopulmonary event with hospital level of care; and
   establishing a communication link between the remote treatment professional and an onsite caregiver to allow the treatment professional to instruct the onsite caregiver how to provide patient treatment corresponding to the alarm signal using the contents of the acute care kit.

2. The method of claim 1 further comprising:
   determining the predetermined threshold prior to monitoring based upon a baseline specific to an individual patient; and
   continuously monitoring the patient for any changes in cardiopulmonary parameters.

3. The method of claim 2, wherein continuously monitoring the patient includes monitoring by one of a lay person and a clinical professional.

4. The method of claim 1, wherein the alarm signal includes a message including the specific location of the patient and an indication that the patient needs immediate attention for diagnosis and treatment.

5. The method of claim 1 further comprising:
transmitting the received cardiopulmonary parameters to a remote database server,
comparing the cardiopulmonary parameters to stored baseline cardiopulmonary parameters for the individual patient, and
notifying a physician upon detection of changes to the cardiopulmonary parameters.

6. The method of claim 1, further comprising:
monitoring symptoms of the patient including at least one of cardiovascular or pulmonary related symptoms;
generating a symptom alarm signal in response to detecting a patient symptom; and
transmitting the symptom alarm signal to the one or more preselected recipients.

7. The method of claim 6, wherein the predetermined threshold indicating a cardiopulmonary event is based on individual parameters and varies between patients.

8. A non-transitory computer-readable medium having stored thereon computer-readable instructions which when executed by a computing device cause the computing device to perform a method of diagnosis, monitoring and testing cardiopulmonary events using an acute care kit comprising:
receiving cardiopulmonary parameters of a patient from (i) one or more subcutaneously embedded sensors including at least an invasive 12-lead ECG or (ii) one or more surface diagnostic hospital grade devices including at least a non-invasive surface 12-lead ECG;
receiving lab or imaging results;
generating an alarm signal when one or more of the cardiopulmonary parameters exceeds a predetermined threshold, the alarm signal being further based on the lab or imaging results and the alarm signal indicating a cardiopulmonary event;
transmitting the alarm signal to a network including a remote treatment professional designated to provide immediate diagnosis and treatment for the cardiopulmonary event; and
establishing a communication link between the remote treatment professional and an onsite caregiver to allow the treatment professional to provide instructions to the onsite caregiver how to provide patient diagnosis and treatment corresponding to the alarm signal using the contents of the acute care kit.

9. A computing device comprising:
processing circuitry configured to
receive cardiopulmonary parameters of a patient from (i) one or more subcutaneously embedded sensors and (ii) one or more diagnostic hospital grade devices including at least a 12-lead ECG;
generate an alarm signal when one or more of the cardiopulmonary parameters exceeds a predetermined threshold, the alarm signal being further based on lab or imaging results and the alarm signal indicating a cardiopulmonary event;
transmit the alarm signal to a network including a remote treatment professional designated to provide immediate diagnosis and treatment for the cardiopulmonary event; and
establish a communication link between the remote treatment professional and on onsite caregiver to allow the treatment professional to provide instructions to the onsite caregiver how to provide patient diagnosis and treatment corresponding to the alarm signal using the contents of an acute care kit.

* * * * *